(12) United States Patent
Kishioka (10) Patent No.: US 8,403,831 B2
(45) Date of Patent: Mar. 26, 2013

(54) ENDOSCOPE APPARATUS WITH MOVEMENT DRIVING MECHANISM FOR DISPLAY

(75) Inventor: Shigeyasu Kishioka, Kunitachi (JP)

(73) Assignee: Olympus Medical Systems Corp. (JP)

( * ) Notice: Subject to any disclaimer, the term of this patent is extended or adjusted under 35 U.S.C. 154(b) by 125 days.

(21) Appl. No.: 13/005,848

(22) Filed: Jan. 13, 2011

(65) Prior Publication Data

US 2011/0208002 A1 Aug. 25, 2011

Related U.S. Application Data

(63) Continuation of application No. PCT/JP2010/060084, filed on Jun. 15, 2010.

(30) Foreign Application Priority Data

Jul. 29, 2009 (JP) ................................. 2009-176669

(51) Int. Cl.
*A61B 1/00* (2006.01)
(52) U.S. Cl. ....................................................... 600/131
(58) Field of Classification Search .................. 600/131, 600/146; 74/22 R
See application file for complete search history.

(56) References Cited

U.S. PATENT DOCUMENTS

| | | | | |
|---|---|---|---|---|
| 5,551,945 | A | * | 9/1996 | Yabe et al. ..................... 600/122 |
| 7,618,413 | B2 | * | 11/2009 | Weitzner et al. .................. 606/1 |
| 2002/0077528 | A1 | * | 6/2002 | Landgraf ...................... 600/131 |
| 2004/0054254 | A1 | | 3/2004 | Miyake |
| 2004/0204628 | A1 | * | 10/2004 | Rovegno ...................... 600/131 |
| 2006/0004258 | A1 | * | 1/2006 | Sun et al. ....................... 600/160 |
| 2007/0106122 | A1 | * | 5/2007 | Yokota et al. .................. 600/188 |
| 2007/0249904 | A1 | | 10/2007 | Amano et al. |
| 2008/0236575 | A1 | | 10/2008 | Chuda |

FOREIGN PATENT DOCUMENTS

| | | |
|---|---|---|
| JP | 62-26042 | 2/1987 |
| JP | 1-155402 | 10/1989 |
| JP | 3-228728 | 10/1991 |
| JP | 5-207965 | 8/1993 |
| JP | 6-54795 | 3/1994 |
| JP | 2002-330926 | 11/2002 |
| JP | 2005-237513 | 9/2005 |
| JP | 2006-43094 | 2/2006 |
| JP | 2008-43726 | 2/2008 |

OTHER PUBLICATIONS

Translation of JP 2006-043094, published Feb. 15, 2006.*
International Search Report and Written Opinion mailed Aug. 3, 2010 in corresponding PCT International Application No. PCT/JP2010/060084.
Search Report issued by European Patent Office on Mar. 1, 2012 in connection with corresponding EP patent application No. EP 10 804 200.3-1265.

* cited by examiner

*Primary Examiner* — John P Leubecker
(74) *Attorney, Agent, or Firm* — Ostrolenk Faber LLP (57) ABSTRACT

An endoscope apparatus includes a display portion coupled to an operation portion, configured to be moved relative to the operation portion and configured to display an observation image obtained by the endoscope apparatus, a bending operation portion provided at the operation portion and configured to be moved in a basic direction relative to the operation portion wherein the bending operation portion is configured to be moved in an additional direction different from the basic direction, and a movement driving mechanism configured to move the display portion relative to the operation portion according to movement of the bending operation portion in the additional direction relative to the operation portion.

4 Claims, 5 Drawing Sheets

ENDOSCOPE APPARATUS WITH MOVEMENT DRIVING MECHANISM FOR DISPLAY

CROSS-REFERENCE TO RELATED APPLICATIONS

This is a Continuation Application of PCT Application No. PCT/JP2010/060084, filed Jun. 15, 2010, which was published under PCT Article 21(2) in Japanese.

This application is based upon and claims the benefit of priority from prior Japanese Patent Application No. 2009-176669, filed Jul. 29, 2009, the entire contents of which are incorporated herein by reference.

BACKGROUND OF THE INVENTION

1. Field of the Invention

The present invention relates to an endoscope apparatus in which a bending portion is configured to be actuated to be bent by operating a bending operation portion and including an actuation portion.

2. Description of the Related Art

Jpn. Pat. Appln. KOKAI Publication No. 2006-43094 discloses an endoscope apparatus in which a bending portion is configured to be actuated to be bent by operating a bending operation lever. That is, an endoscope includes an elongated insertion portion configured to be inserted into a lumen. A bending portion is provided at the distal end portion of the insertion portion and configured to be actuated to be bent. An operation portion is coupled to the proximal end portion of the insertion portion and configured to be held and operated by an operator. A bending operation lever is provided at the operation portion and configured to actuate the bending portion to be bent. When the endoscope is used, the operation portion is held with the one hand, the finger or the thumb of the one hand is placed on the bending operation lever, and the bending operation lever is operated by the finger or the thumb, whereby the bending portion is actuated to be bent.

BRIEF SUMMARY OF THE INVENTION

In an aspect of the present invention, an endoscope apparatus includes: an insertion portion configured to be inserted into a lumen; an operation portion coupled to the insertion portion and configured to be held and operated by an operator; and a display portion coupled to the operation portion, configured to be moved relative to the operation portion and configured to display an observation image obtained by the endoscope apparatus, and the endoscope apparatus includes: a bending portion provided at the insertion portion and configured to be actuated to be bent; a bending operation portion provided at the operation portion and configured to be moved in a basic direction relative to the operation portion wherein the bending operation portion is configured to be moved in an additional direction different from the basic direction; a bending driving mechanism configured to actuate the bending portion to be bent according to movement of the bending operation portion in the basic direction relative to the operation portion; and a movement driving mechanism configured to move the display portion relative to the operation portion according to movement of the bending operation portion in the additional direction relative to the operation portion.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Each of embodiments of the present invention will be explained with reference to the drawings.

Referring to FIGS. 1 to 5, a first embodiment of the present invention will be explained.

Referring to FIGS. 1 to 4, a carrying type of endoscope with a monitor 16 according to the present embodiment will be explained.

The endoscope 16 includes an elongated insertion portion 17 configured to be inserted into a cavity in the body. A distal rigid portion being rigid, a bending portion 19 configured to be actuated to be bent in two directions, that is, upward and downward, and a flexible tube portion being long and flexible are connected from the distal end side to the proximal end side in the insertion portion 17. An operation portion 24 is coupled to the proximal end portion of the insertion portion 17 and configured to be held and operated by an operator. The operation portion 24 extends in longitudinal directions. Hereinafter, directions orthogonal to the longitudinal directions are referred to as wide directions, directions orthogonal to both the longitudinal directions and the wide directions are referred to as thick directions, and one side and the other side in the thick directions are referred to as a front side and a back side, respectively, in the operation portion 24. A holding portion 26 is formed at the distal end side part of the operation portion 24 and configured to be held by an operator. The holding portion 26 has a shape of a thick rod extending in the longitudinal directions. An operation portion main portion 27 is formed at the proximal end side part of the operation portion 24 and configured to be operated by the operator. A bending operation lever 28 is provided at the operation portion main portion 27 and configured to operate the bending portion 19 to be bent.

A camera unit 29 is coupled to the proximal end portion of the operation portion 24. As is shown by an arrow U in FIG. 4, the whole camera unit 29 is configured to be rotated about a rotational axis relative to the operation portion 24. That is, the camera unit 29 is formed by a camera main portion 31 on the distal end side and a monitor portion 32 on the proximal end side. The camera main portion 31 is coupled to the operation portion 24. The camera main portion 31 has a shape of a flat rectangular parallelepiped substantially orthogonal to the longitudinal directions of the operation portion 24. A rotation supporting mechanism is formed between the operation portion 24 and the camera main portion 31, and the camera main portion 31 is configured to be rotated about a rotational axis substantially parallel to the longitudinal directions of the operation portion 24, relative to the operation portion 24. Here, front surface, back surface, one side surface and other side surface of the camera main portion 31 are displaced to face front side and back side in the thick directions and one side and other side in the wide directions of the operation portion 24, respectively, when the camera main portion 31 is in normal position relative to the operation portion 24.

The monitor portion 32 is coupled to the camera main portion 31. As is shown by an arrow T in FIG. 4, the monitor portion 32 is configured to be tilted about a tilting axis orthogonal to the rotational axis relative to the camera main portion 31. That is, the monitor portion 32 has a shape of a flat rectangular parallelepiped. The monitor portion 32 is displaced to be overlapped with the camera main portion 31 in the rotationally axial direction, and the front surface, the back surface, the one side surface and the other side surface of the monitor portion 32 are displaced to be aligned with the front surface, the back surface, the one side surface and the other side surface of the camera main portion 31, respectively, when the monitor portion 32 is in normal position relative to the camera main portion 31. A tilt supporting mechanism is formed between the camera main portion 31 and the monitor portion 32. That is, a notch-shaped housing portion 33 is formed at the corner portion on the front and other side surface side and extends over the whole length in the rotationally axial direction in the camera main portion 31. A pivot receiving wall 34 is formed at the housing portion 33 and faces toward the other side surface side. On the other hand, a protruding portion 36 protrudes at the corner portion on the front and other side surface side in the distal end surface portion of the monitor portion 32. A pivot wall 37 is formed at the protruding portion 36 and faces the one side surface side. The protruding portion 36 of the monitor portion 32 is housed within the housing portion 33 of the camera main portion 31, and the pivot wall 37 of the protruding portion 36 is displaced to face the pivot receiving wall 34 of the housing portion 33. The pivot axis portion 38 protrudes from the pivot wall 37 of the protruding portion 36 substantially parallel to the front surface of the monitor portion 32 and toward the one side surface side, and the pivot axis portion 38 is supported by a housing 63 of the camera main portion 31 and configured to be rotated about the central axis of the pivot axial portion 38. The protruding portion 36 is configured to be tilted about a tilting axis substantially orthogonal to the rotational axis of the camera main portion 31 and substantially parallel to the front surface of the camera main portion 31. The monitor portion 32 is configured to be raised up toward the front side relative to the camera main portion 31 by tilting the monitor portion 32 relative to the camera main portion 31 when the camera main portion 31 is in the normal position relative to the operation portion 24.

Figure 1:
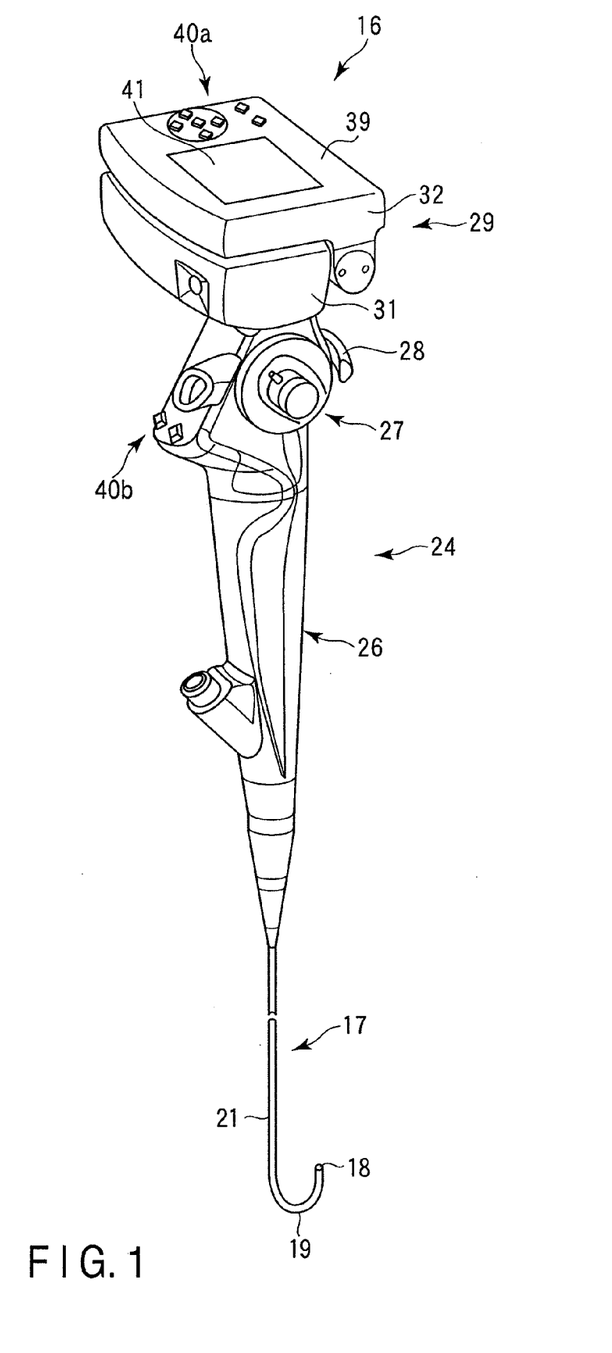
FIG. 1 is a perspective view showing from the back side an endoscope according to a first embodiment of the present invention.
Figure 2:
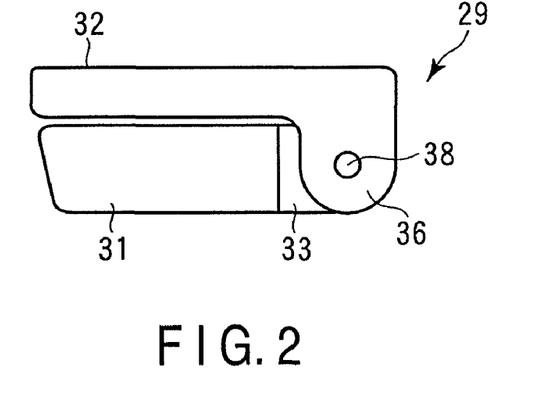
FIG. 2 is a side view showing a camera unit according to the first embodiment of the present invention.
Figure 3:
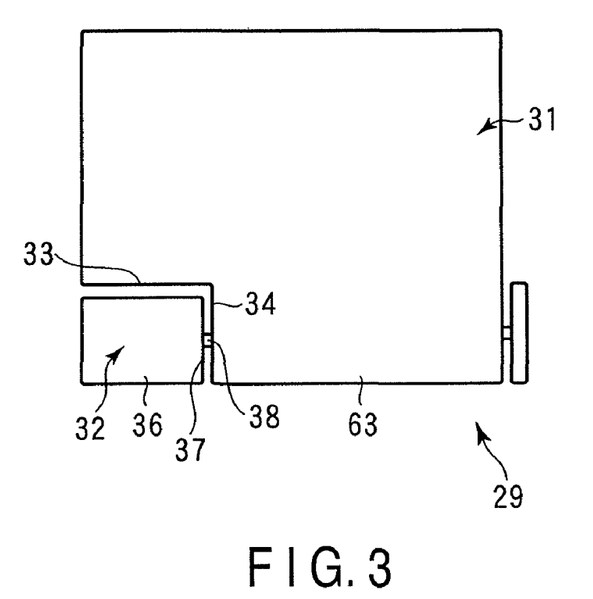
FIG. 3 is a top view showing the camera unit according to the first embodiment of the present invention.
Figure 4:
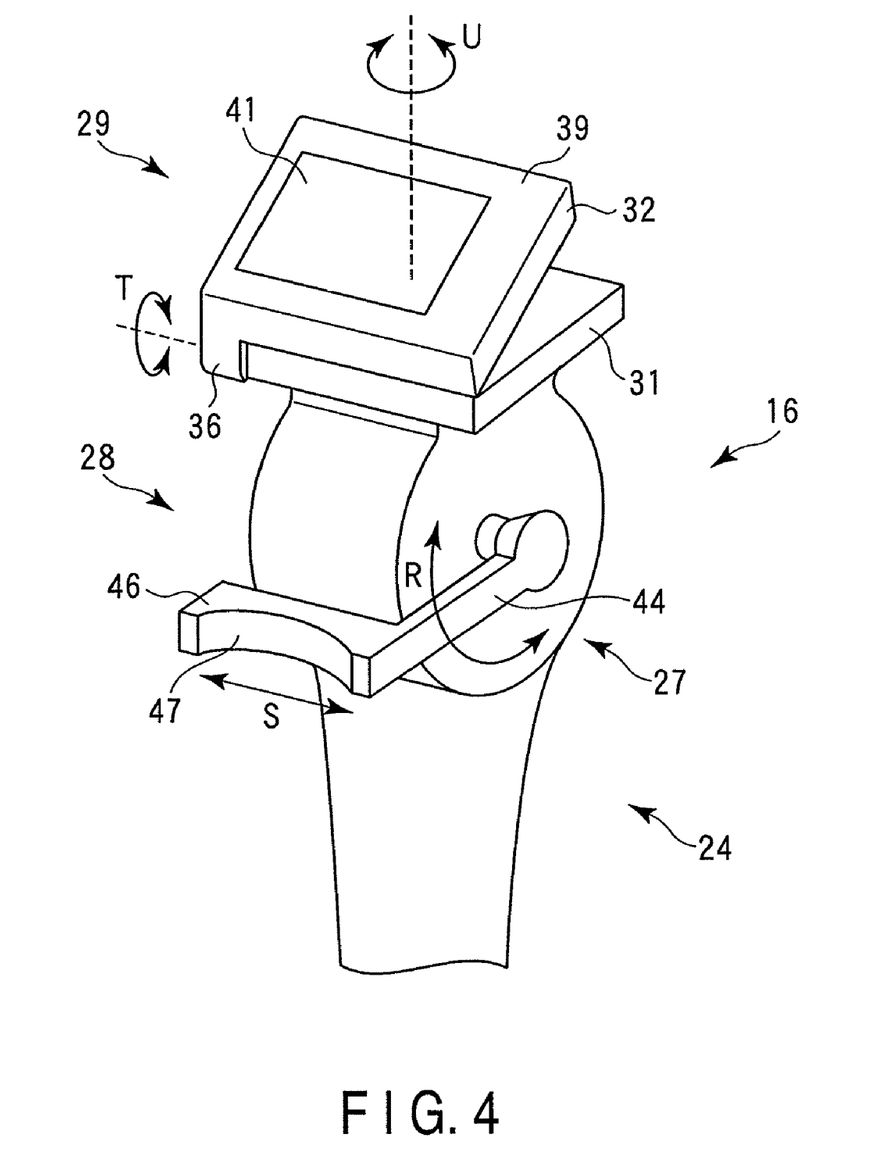
FIG. 4 is a perspective view showing from the front side an operation portion according to the first embodiment of the present invention.

The distal end surface of the monitor portion 32 forms an operation display surface 39. A liquid crystal monitor 41 and various switches 40a are provided at the operation display surface 39, the liquid crystal monitor 41 is configured to display an observation image and the various switches 40a is configured to operate the camera unit 29. Here, various switches 40b configured to operate the camera unit 29 is provided at the operation portion main portion 27 of the operation portion 24, too.

Figure 5:
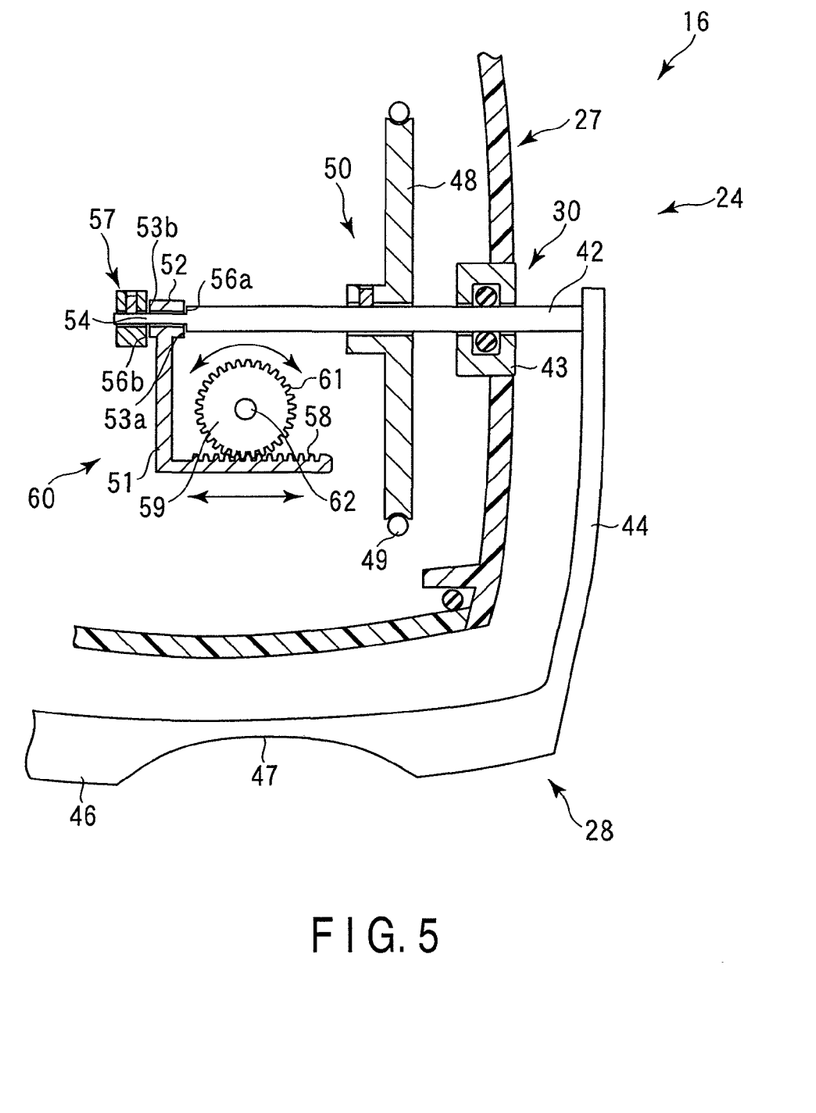
FIG. 5 is a transverse cross-sectional view showing an operation portion main portion according to the first embodiment of the present invention.

Referring to FIGS. 4 and 5, features of the endoscope 16 will be explained in detail.

A supporting mechanism 30 will be explained which supports the bending operation lever 28 such that the bending operation lever 28 is rotatable in the longitudinal directions of the operation portion 24 as basic directions and slidable in the wide directions as additional directions of the operation portion 24.

A supporting axis portion 42 is displaced in the operation portion main portion 27 and passes through one side wall of the operation portion main portion 27. An axis receiving portion 43 is formed at the one side wall of the operation portion main portion 27. The supporting axis portion 42 is displaced substantially parallel to the wide directions of the operation portion 24, and supported by the axis receiving portion 43 such that the supporting axis portion 42 is rotatable about the central axis of the supporting axis portion 42 and slidable in the axial direction of the supporting axis portion 42. The bending operation lever 28 as a bending operation portion is coupled to the outer end portion of the supporting axis portion 42. The bending operation lever 28 is formed by a coupling portion 44 on the root side and an operation receiving portion 46 on the terminal end portion. The root end portion of the coupling portion 44 is coupled to the outer end portion of the supporting axis portion 42. The coupling portion 44 extends from the back side to the front side in the thick directions of the operation portion 24 from the root end portion to the terminal end portion thereof when the bending operation lever 28 is in neutral position. The root end portion of the operation receiving portion 46 is coupled to the terminal end portion of the coupling portion 44. The operation receiving portion 46 extends in the wide directions from the root end portion to the terminal end portion thereof when the bending operation lever 28 is in the neutral position. A concave finger placement portion 47 is formed at the front surface portion of the operation receiving portion 46, on which the thumb is to be placed. As is mentioned above, the supporting axis portion 42 is supported by the axis receiving portion 43 such that the supporting axis portion 42 is rotatable about the central axis of the supporting axis portion 42 and slidable in the axial directions of the supporting axis portion 42. Thus, the bending operation lever 28 is configured to be rotated in the longitudinal directions relative to the operation portion 24 about a rotational axis corresponding with the central axis of the supporting axis portion 42 and extending in the wide directions, as is shown by an arrow R in FIG. 4. Moreover, the bending operation lever 28 is configured to be slid in the wide directions relative to the operation portion 24, as is shown by an arrow S in FIG. 4. That is, the supporting mechanism 30 is formed by the supporting axis portion 42 and the axis receiving portion 43.

A bending driving mechanism 50 will be explained which is configured to actuate the bending portion 19 to be bent according to rotation of the bending operation lever 28 in the longitudinal directions.

An angle drum 48 has a shape of a circular plate including a central bore and is fitted on the outside of the axially middle part of the supporting axis portion 42 and fixed thereto by a fixing screw in the operation portion main portion 27. An angle wire 49 is wound around the outer peripheral portion of the angle drum 48. One end side part and the other end side part of the angle wire 49, which extend from the angle drum 48, are inserted through the operation portion 24 and the insertion portion 17, displaced at the upper position and the lower position, respectively, in the bending portion 19 and fixed in the distal end portion of the bending portion 19. The supporting axis portion 42 and the angle drum 48 are configured to be rotated in one direction, the one end side part and the other end side part of the angle wire 49 are configured to be pulled and loosened, and the bending portion 19 is configured to be actuated to be bent upward, by operating the bending operation lever 28 to be rotated in the one longitudinal direction. Similarly, the bending portion 19 is configured to be actuated to be bent downward by operating the bending operation lever 28 to be rotated in the other longitudinal direction.

A rotation driving mechanism 60 as a driving unit and a movement driving mechanism will be explained which is configured to actuate the monitor portion 32 as an actuation portion and a display portion to be rotated relative to the operation portion 24 according to slide of the bending operation lever 28 in the wide directions.

A rack 51 is provided within the operation portion main portion 27. The rack 51 has an L-shape when viewed in the longitudinal directions of the operation portion 24 and is formed by the one end side part extending in the thick directions of the operation portion 24 and the other end side part extending in the wide directions thereof. Moreover, the rack 51 is supported such that the rack 51 is slidable in the wide directions.

A rack connecting portion 52 is formed at the one end portion of the rack 51 and has a shape of a circular cylinder extending in the wide directions. On the other hand, an axis portion connecting portion 54 is formed at the axially inner end portion of the supporting axis portion 42 of the bending operation lever 28, and the inner diameter thereof is decreased. The rack connecting portion 52 having a shape of a circular cylinder is fitted on the outside of the axis portion connecting portion 54 having a shape of a circular column, and the axis portion connecting portion 54 is configured to be rotated about the central axis of the supporting axis portion 42 relative to the rack connecting portion 52. That is, the rack 51 is configured not to prevent rotation of the supporting axis portion 42, that is, rotation operation for the bending operation lever 28.

Moreover, a first driving receiving surface 53s and a second driving receiving surface 53b are formed by the outer end surface and the inner end surface in the wide directions, of the rack connecting portion 52 in the rack 51, respectively. On the other hand, a step surface is formed at the outer end portion in the wide directions, of the axis portion connecting portion 54, and a first driving surface 56a is formed by the step surface in the bending operation lever 28. Moreover, a restricting member 57 has a shape of a circular plate including the central bore, and is fitted on the outside of the inner end portion in the wide directions, of the axis portion connecting portion 54 and fixed thereto by a fixing screw. A second driving surface 56b is formed by the outer end surface in the wide directions, of the restricting member 57. The first driving receiving surface 53a and the second driving receiving surface 53b of the rack connecting portion 52 are displaced to face the first driving surface 56a of the restricting member 57 and the second driving surface 56b of the supporting axis portion 42 with slight clearances, respectively. The first driving receiving surface 53a and the second driving receiving surface 53b of the rack connecting portion 52 are configured to be driven in the one wide direction and the other wide direction by the second driving surface 56b of the restricting member 57 and the first driving surface 56a of the supporting axis portion 42, respectively, and the rack 51 is configured to be moved in the one wide direction and the other wide direction by operating the bending operation lever 28 to be slid in the one wide direction and the other wide direction, respectively.

A rack teeth portion 58 extends in the wide directions, at the back side part in the thick directions, in the other end side part of the rack 51. A pinion teeth portion 61 of a pinion 59 is engaged with the rack teeth portion 58. A coupling axis portion 62 is coaxially coupled to the pinion 59, and the coupling axis portion 62 is coupled to the camera main portion 31 of the camera unit 29. The pinion 59 is configured to be rotated in one direction and the other direction due to interaction between the rack teeth portion 58 and the pinion teeth portion 61 by moving the rack 51 in the one wide direction and the other wide direction, and the camera main portion 31 is configured to be actuated to be rotated in the one direction and the other direction about the rotational axis relative to the operation portion 24 via the coupling axis portion 62, respectively.

Next, a method for using the endoscope 16 according to the present embodiment will be explained.

When the endoscope 16 is used, the endoscope 16 is displaced such that the endoscope 16 extends in up and down direction relative to a medical doctor and the front side thereof faces the medical doctor, the holding portion 26 of the operation portion 24 is enclosed from the one side in the wide direction and held with the four fingers other than the thumb of the one hand, and the thumb of the one hand is displaced on the front side of the operation portion 24 and placed on the finger placement portion 47 of the bending operation lever 28. The camera unit 29 is appropriately actuated to be rotated relative to the operation portion 24, and also, the monitor portion 32 is appropriately actuated to be tilted relative to the camera main portion 31, whereby the liquid crystal monitor 41 of the monitor portion 32 is displaced such that it is easy to visually confirm the liquid crystal monitor 41. In the state where the operation portion 24 is held with the one hand and the thumb of the one hand is placed on the bending operation lever 28, the whole operation portion 24 is operated, whereby the whole endoscope 16 is actuated to be advanced and retreated in the longitudinal directions and rotated about the central axis of the endoscope 16, and also, the bending operation lever 28 is operated to be rotated in the longitudinal directions of the operation portion 24 with the thumb, whereby the bending portion 19 is actuated to be bent. By these actuations, the insertion portion 17 of the endoscope 16 is inserted into a cavity in the body, a field of view of the endoscope 16 is moved and an object of observation is disposed within the field of view, and the object of observation is observed via an observation image displayed on the liquid crystal monitor 41. In the present embodiment, in particular, since the bending portion 19 can be actuated to be bent only in the two directions, that is, upward and downward, it is necessary to actuate the endoscope 16 to be rotated about the central axis of the endoscope 16 in order to make the distal end portion of the insertion portion 17 in a desired orientation. Here, when the endoscope 16 is actuated to be rotated about the central axis of the endoscope 16, the orientation of the liquid crystal monitor 41 may be changed to an orientation in which it is hard for the medical doctor to visually confirm the liquid crystal monitor 41. Moreover, when the observation image is shown to an assistant and others other than the medical doctor, it may be necessary to turn the liquid crystal monitor 41 toward the assistant and others. In this case, the bending operation lever 28 is operated to be slid in the wide directions of the operation portion 24 with the thumb, whereby the camera unit 29 is actuated to be rotated about the rotational axis relative to the operation portion 24 and the liquid crystal monitor 41 of the monitor portion 32 is again displaced in an orientation in which it is easy to visually confirm the liquid crystal monitor 41, while the operation portion 24 is held with the one hand and the thumb of the one hand is placed on the bending operation lever 28.

The endoscope 16 according to the present embodiment has following effects.

In the endoscope 16 according to the present embodiment, the bending portion 19 can be actuated to be bent by holding the operation portion 24 with the one hand, placing the thumb of the one hand on the bending operation lever 28 and operating the bending operation lever 28 to be rotated in the longitudinal directions of the operation portion 24, and furthermore, the liquid crystal monitor 41 of the monitor portion 32 can be displaced in an orientation in which it is easy to visually confirm the liquid crystal monitor 41 by operating the bending operation lever 28 to be slid in the wide directions of the operation portion 24 to actuate the camera unit 29 to be rotated about the rotational axis substantially parallel to the longitudinal axis of the operation portion 24. That is, in the state where the operation portion 24 is held with the one hand and the thumb of the one hand is placed on the bending operation lever 28, the liquid crystal monitor 41 of the monitor portion 32 can be displaced in an orientation in which it is easy to visually confirm the liquid crystal monitor 41. Therefore, visibility of the liquid crystal monitor 41 is improved without making operability of the endoscope 16 worse. Moreover, operation for actuating the bending portion 19 to be bent is similar to that in a conventional endoscope, and therefore, even an operator experienced at the conventional endoscope can operate without an unhandy feeling.

Figure 6:
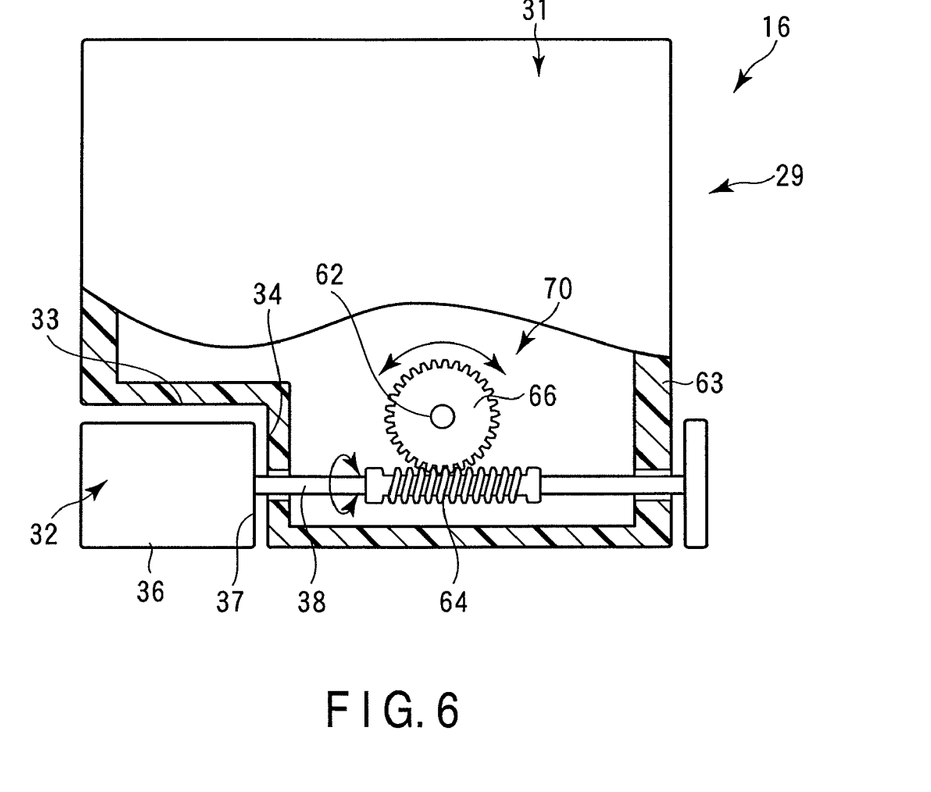
FIG. 6 is a partially transversally cross-sectional top view showing a camera unit according to a second embodiment of the present invention.

Referring to FIG. 6, a second embodiment of the present invention will be explained.

An endoscope 16 according to the present embodiment does not include a rotation supporting mechanism and a rotation driving mechanism 60 such as those according to the first embodiment but includes instead a tilt driving mechanism 70 configured to actuate a monitor portion 32 to be tilted relative to a camera main portion 31 according to slide of a bending operation lever 28 in wide directions.

As is mentioned above, a pivot axial portion 38 protrudes from a protruding portion 36 of the monitor portion 32, and the pivot axial portion 38 is supported so as to be rotated about the central axis of the pivot axial portion 38 by a housing 63 of the camera main portion 31. On the other hand, the tilt driving mechanism 70 includes a similar mechanism to the rotation driving mechanism 60 shown in FIG. 5 in an operation portion main portion 27. In addition, a coupling axis portion 62 is inserted into the camera main portion 31. A worm gear 66 is coaxially coupled to the coupling axis portion 62 in the camera main portion 31. A worm 64 is engaged with the worm gear 66. The worm 64 is cylindrical, and the pivot axial portion 38 is fitted on the inside of and coupled to the worm 64. The coupling axis portion 62 and the worm gear 66 are configured to be rotated in one direction and the other direction due to similar actuation to that of the first embodiment by operating the bending operation lever 28 to be slid in the one wide direction and the other wide direction, to the worm 64 and the pivot axial portion 38 to be rotated in one direction and the other direction about the central axis of the pivot axial portion 38 relative to the housing 63 of the camera main portion 31, respectively. The monitor portion 32 is configured to be actuated to be tilted in one direction and the other direction about a tilting axis relative to the camera main portion 31 by rotation of the pivot axial portion 38 in one direction and the other direction, respectively.

Here, a spur gear and a bevel gear may be used instead of the worm gear 66 and the worm 64.

When the endoscope 16 is used, the endoscope 16 is displaced such that the endoscope 16 extends in the up and down direction relative to a medical doctor and the front side thereof faces the medical doctor. In the state where the operation portion 24 is held with the one hand and the thumb of the one hand is placed on the bending operation lever 28, the whole operation portion 24 is operated, whereby the whole endoscope 16 is actuated to be advanced and retreated in the longitudinal direction. At this time, since the liquid crystal monitor 41 is moved in the up and down direction relative to the medical doctor, it may be hard for the medical doctor to visually confirm the liquid crystal monitor 41 depending on a tilting angle of the monitor portion 32. Moreover, when an observation image is shown to an assistant and others other than the medical doctor, it may be necessary to turn the liquid crystal monitor 41 toward the assistant and others. In this case, the bending operation lever 28 is operated to be slid in the wide directions of the operation portion 24 with the thumb, whereby the monitor portion 32 is actuated to be tilted about the tilting axis relative to the camera main portion 31 such that it is easy to visually confirm the liquid crystal monitor 41 of the monitor portion 32 while the operation portion 24 is held with the one hand and the thumb of the one hand is placed on the bending operation lever 28.

The endoscope 16 according to the present invention has similar effects to those of the endoscope 16 according to the first embodiment.

In the above embodiment, a mechanism is used as a rotation driving mechanism, which is configured to directly and mechanically convert sliding operation for a bending operation lever in the wide directions into rotational actuation of a camera unit relative to the operation portion. However, any mechanism may be used as the rotation driving mechanism. For example, the sliding operation of the bending operation lever may be to be detected by a detection switch, and the camera unit may be configured to be driven to be rotated by an electric driving mechanism on the basis of the result of the detection by the detection switch. The same is true of a tilt driving mechanism.

Moreover, in the above embodiment, a rotational function of a camera unit relative to an operation portion and a tilting function of a monitor portion relative to a camera main portion are selected as an object of operation by sliding operation in the wide directions for a bending operation lever. However, a function which is an object of operation is not limited to these functions. Various functions may be selected as an object of operation, which it is desired that can be operated in the state where the operation portion is held with the one hand and the thumb is placed on the bending operation lever.

For example, in a carrying type of endoscope with a monitor, brightness of a liquid crystal monitor is configured to be adjusted by an adjusting switch provided at an operation display surface. In this endoscope, the brightness of the liquid crystal monitor may be adjusted by the sliding operation for the bending operation lever in the wide directions.

In an electric endoscope apparatus, an imaging unit is provided within the distal end portion of an insertion portion and configured to image an observation image, and zoom, focus, exposure compensation and so on are performed by operating various switches provided at an operation portion. In this endoscope apparatus, the zoom, the focus, the exposure compensation and so on may be performed by the above operation.

In an endoscope apparatus, various photometric modes are used as a mode for measuring brightness of an observation image, and the photometric modes are changed with each other by operating a photometric mode changeover switch provided at an operation portion. In this endoscope, the photometric modes may be changed with each other by the above operation.

In an endoscope apparatus, visible light for normal observation, excitation light or infrared light for special observation and the like are produced in a light source apparatus, each of the various lights is transmitted through a light guide inserted through an endoscope and radiated to an object of observation from an illumination optical system in the distal end portion of the insertion portion, and an observation image is imaged by each of an imaging element for the normal observation and an imaging element for the special observation provided within the distal end portion of the insertion portion. The lights produced in the light source are to be changed with each other, the imaging units to be used are to be changed with each other, and observation modes are to be changed with each other by operating an observation mode changeover switch provided at the operation portion. In this endoscope, the observation modes may be changed with each other by the above operation.

In an endoscope apparatus, water is send to an observation window and an illumination window, and the observation window and the illumination window are cleaned in the distal end portion of an insertion portion. The water sending actuation is to be started by operating a water sending switch provided at an operation portion. In this endoscope, the water sending actuation may be to be started by the above operation.

In an endoscope, a bending operation lever is configured to be locked and released relative to an operation portion by operating a lock lever provided at the operation portion to enable the bending operation lever to be rotated and disable the bending operation lever from being rotated in the longitudinal directions relative to the operation portion. A bending state of a bending portion is to be kept by disabling the bending operation lever from being rotated. In this endoscope, the bending operation lever may be configured to be locked and released relative to the operation portion by the above operation.

In an endoscope, a bending portion is configured to be actuated to be bent in four directions, that is, upward, downward, leftward and rightward, the bending portion is configured to be actuated to be bent in the two directions, that is, upward and downward by operating a bending operation lever to be rotated in the longitudinal directions of an operation portion, and the bending portion is configured to be actuated to be bent in the two directions, that is, leftward and rightward by operating a bending operation dial and so forth different from the bending operation lever. In this endoscope, the bending portion may be configured to be actuated to be bent in the two directions, that is, upward and downward by operating the bending operation lever to be rotated in the longitudinal directions, and the bending portion may be configured to be actuated to be bent in the two directions, that is, leftward and rightward by operating the bending operation lever in the wide directions.

In an endoscope, hardness of an insertion portion is adjustable. That is, a coil is inserted through the insertion portion, and an operation wire is inserted through the coil. The wire is configured to be pulled and released to compress and reset the coil to adjust the hardness of the coil, whereby the hardness of the insertion portion is to be adjusted, by operating a hardness adjusting lever provided at an operation portion. In this endoscope, the operation wire is configured to be pulled and released to adjust the hardness of the insertion portion by the above operation.

In an endoscope, an insertion portion is configured to be rotated about the central axis of the insertion portion relative to an operation portion, and the insertion portion is to be rotated relative to the operation portion with the one hand while the operation portion is held with the other hand. In this endoscope, the insertion portion is configured to be actuated to be rotated relative to the operation portion by the above operation.

In an endoscope, a treatment instrument is to be inserted through a treatment instrument channel provided at the endoscope, and projected from and retracted into the distal end portion of an insertion portion, an elevator provided at a treatment instrument projecting opening is configured to be actuated to be rotated to adjust an projecting direction of the treatment instrument by operating an elevator operation lever provided at the operation portion. In this endoscope, the elevator is configured to be actuated to be rotated to adjust the projecting direction of the treatment instrument by the above operation.

In an endoscope, a balloon provided at the distal end portion of an insertion portion is configured to be expanded and shrunk by operating a switch provided at an operation portion to engage and release the balloon with and from the inner surface of a cavity in the body. In this endoscope, the balloon is configured to be expanded and shrunk by the above operation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
an insertion portion configured to be inserted into a lumen;
an operation portion coupled to the insertion portion and configured to be held and operated by an operator; and
a display portion coupled to the operation portion, configured to be moved relative to the operation portion and configured to display an observation image obtained by the endoscope apparatus, and
the endoscope apparatus includes:
a bending portion provided at the insertion portion and configured to be actuated to be bent;
a bending operation portion provided at the operation portion and configured to be moved in a basic direction relative to the operation portion wherein the bending operation portion is configured to be moved in an additional direction different from the basic direction;
a bending driving mechanism configured to actuate the bending portion to be bent according to movement of the bending operation portion in the basic direction relative to the operation portion; and
a movement driving mechanism configured to move the display portion relative to the operation portion according to movement of the bending operation portion in the additional direction relative to the operation portion, wherein
the operation portion forms a longitudinal direction forming the basic direction and a wide direction orthogonal to the longitudinal direction and forming the additional direction, and includes a supporting mechanism supporting the bending operation portion,
the bending operation portion includes:
a coupling portion arranged along directions orthogonal to the longitudinal direction and the wide direction; and
an operation receiving portion coupled to an end portion of the coupling portion, extending in the wide direction and configured to be operated by the operator, and
the supporting mechanism includes:
a supporting axis portion coupled to the other end portion of the coupling portion outside the operation portion and the movement driving mechanism inside the operation portion, and arranged substantially parallel to the operation receiving portion and the wide direction; and an axis receiving portion which supports the supporting axis portion so that the supporting axis portion rotates about a center axis of the supporting axis portion substantially parallel to the wide direction by moving the bending operation portion in the basic direction, and so that the supporting axis portion slides in the wide direction by moving the bending operation portion in the additional direction, wherein the sliding of the supporting axis portion causes the movement driving mechanism to move the display portion relative to the operation portion.

2. The endoscope apparatus according to claim 1, wherein the operation receiving portion includes a finger placement portion having a concave shape and on which a finger or a thumb of the operator is to be placed to slide the bending operation portion in the wide direction relative to the operation portion.

3. The endoscope apparatus according to claim 1,
wherein the display portion is configured to be rotated about a rotational axis substantially parallel to the longitudinal direction relative to the operation portion, and
the movement driving mechanism includes a rotation driving mechanism configured to rotate the display portion relative to the operation portion according to movement of the bending operation portion in the additional direction relative to the operation portion.

4. The endoscope apparatus according to claim 1,
wherein the display portion is configured to be tilted about a tilting axis substantially parallel to the wide direction relative to the operation portion, and
the movement driving mechanism includes a tilt driving mechanism configured to tilt the display portion relative to the operation portion according to movement of the bending operation portion in the additional direction relative to the operation portion.

* * * * *